(12) United States Patent  (10) Patent No.: US 8,188,446 B2
Ohno  (45) Date of Patent: May 29, 2012

(54) FLUORESCENCE IMAGING APPARATUS

(75) Inventor: Wataru Ohno, Tokyo (JP)

(73) Assignee: Olympus Corporation, Tokyo (JP)

( * ) Notice: Subject to any disclaimer, the term of this patent is extended or adjusted under 35 U.S.C. 154(b) by 190 days.

(21) Appl. No.: 12/531,604

(22) PCT Filed: Mar. 14, 2008

(86) PCT No.: PCT/JP2008/054799
§ 371 (c)(1),
(2), (4) Date: Sep. 16, 2009

(87) PCT Pub. No.: WO2008/114748
PCT Pub. Date: Sep. 25, 2008

(65) Prior Publication Data
US 2010/0084563 A1    Apr. 8, 2010

(30) Foreign Application Priority Data
Mar. 20, 2007  (JP) ................................. 2007-073391

(51) Int. Cl.
*G01N 21/64* (2006.01)
(52) U.S. Cl. ..................... 250/461.1; 600/476; 600/564; 600/407
(58) Field of Classification Search ............. 600/476, 600/564, 407; 250/461.1
See application file for complete search history.

(56) References Cited

U.S. PATENT DOCUMENTS

| 5,507,287 A | 4/1996 | Palcic et al. |
| 5,827,190 A | 10/1998 | Palcic et al. |
| 5,833,617 A * | 11/1998 | Hayashi ........................ 600/476 |
| 6,174,291 B1 * | 1/2001 | McMahon et al. ............ 600/564 |
| 2006/0058611 A1 * | 3/2006 | Descour et al. ............... 600/407 |
| 2007/0016077 A1 | 1/2007 | Nakaoka et al. |

FOREIGN PATENT DOCUMENTS

| JP | 6-54792 | 3/1994 |
| JP | 9-308604 | 12/1997 |
| JP | 2001-190489 | 7/2001 |
| JP | 3683271 | 6/2005 |
| JP | 2006-187598 | 7/2006 |

* cited by examiner

*Primary Examiner* — David Porta
*Assistant Examiner* — Hugh H Maupin
(74) *Attorney, Agent, or Firm* — Scully, Scott, Murphy & Presser, P.C.

(57) ABSTRACT

The distribution of abnormal tissue, such as lesions, in an observed object is precisely detected regardless of the distribution of absorbing material present in a living organism. Provided is a fluorescence imaging apparatus (1) including an excitation-light radiating unit (2) that irradiates an observed object with excitation light of a plurality of wavelengths; a filter (14) that transmits fluorescence in a specific wavelength band from among fluorescence produced by the observed object in response to the excitation light radiated from the excitation-light radiating unit (2); a light detector (15) that detects the fluorescence transmitted through the filter (14); and a computing unit (18) that calculates a fluorescence intensity ratio in the same wavelength band in response to the excitation light of the plurality of wavelengths, which is detected by the light detector (15).

12 Claims, 10 Drawing Sheets

FLUORESCENCE IMAGING APPARATUS

TECHNICAL FIELD

The present invention relates to a fluorescence imaging apparatus.

BACKGROUND ART

In endoscopic observation of living organisms using an endoscope system, in order to precisely observe the state of the living organism, it is preferable to implement an observation method utilizing a plurality of kinds of light with different spectral characteristics.

Endoscopes that are capable of observation using a plurality of kinds of light with different spectral characteristics are disclosed in Patent Document 1 and Patent Document 2.

With the endoscope disclosed in Patent Document 1, in order to acquire a plurality of kinds of images by using the plurality of kinds of light with different spectral characteristics in the same endoscope, light from the acquired object is spectrally separated by a dichroic mirror. Because it is difficult to build the dichroic mirror into the tip of an insertion portion of the endoscope, it is disposed outside the body, and it is thus necessary to convey the light from the acquired object, which is received at the tip of the insertion portion, to the dichroic mirror outside the body via a fiber bundle.

The endoscope disclosed in Patent Document 2 is capable of observation using a plurality of kinds of light without employing spectral means such as a dichroic mirror, and therefore, a plurality of image-acquisition optical systems are disposed at the tip of the insertion portion of the endoscope.

Furthermore, from commercially available fluorescent agents, it is possible to produce fluorescent probes that emit light upon binding to material in a living organism; and by administering the living organism with a fluorescent probe that binds to a material related to a lesion and observing the fluorescence therefrom, it is possible to obtain information about the lesion.

Patent Document 1: Publication of Japanese Patent No. 3683271

Patent Document 2: Japanese Unexamined Patent Application, Publication No. 2001-190489

DISCLOSURE OF INVENTION

When observing autofluorescence from an autofluorescent substance that is naturally present in biological tissue, fluorescence in multiple wavelength bands may be excited with one kind of excitation light. In this case, it is possible to more precisely observe the state of the living organism by separating and detecting the fluorescences.

However, because material that absorbs light is also present in biological tissue, in addition to the material that emits fluorescence, it is difficult to precisely detect the distribution of the fluorescent material due to the distribution of this absorbing material.

A fluorescence imaging apparatus is provided for precisely detecting the distribution of abnormal tissue, such as lesions, in an observed object regardless of the distribution of absorbing material present in a living organism.

One aspect of a fluorescence imaging apparatus according to the present invention is a fluorescence imaging apparatus including an excitation-light radiating unit that irradiates an observed object with excitation light of a plurality of wavelengths; a filter that transmits fluorescence in a specific wavelength band from among fluorescence produced from the observed object in response to the excitation light radiated from the excitation-light radiating unit; a light detector that detects the fluorescence transmitted through the filter; and a computing unit that calculates a fluorescence intensity ratio in the same wavelength band in response to the excitation light of the plurality of wavelengths, which is detected by the light detector.

In the above-described aspect, the filter may transmit fluorescence of a plurality of wavelength bands, and the computing unit may calculate the fluorescence intensity ratio in each wavelength band.

In the above-described aspect, the filter may be formed of a variable spectrum element that can change the wavelength band at which the fluorescence is transmitted.

The above-described aspect may be configured such that the wavelength of at least one kind of excitation light of the excitation light of the plurality of wavelengths is contained in a wavelength band between a maximum-excitation wavelength of a first substance excited by the excitation light and a maximum-excitation wavelength of a second substance that differs from the first substance.

In the above-described aspect, the first substance may be collagen or NADH, and the second substance may be FAD.

In the above-described aspect, the wavelength of at least one kind of excitation light in the excitation light of the plurality of wavelengths may contain a wavelength with a middle value between the maximum-excitation wavelength of the first substance excited by the excitation light and the maximum-excitation wavelength of the second substance that differs from the first substance.

In the above-described aspect, the pass band of the filter that transmits the fluorescence with a specific wavelength band may contain a wavelength at which the fluorescence intensity of collagen, NADH, FAD, or porphyrin is maximized.

In the above-described aspect, the variable spectrum element may shift a transmission band that is narrower than the wavelength band for detecting fluorescence, and the computing unit may calculate the ratio using integrated values of the fluorescence intensities detected by the light detector at each shifted position of the transmission band.

In the above-described aspect, the computing unit may calculate the fluorescence intensity ratio according to the following expression.

$$(EM1ex1/EM1ex2)/(Em2ex3/EM2ex2)$$

Here, EM1ex1 is the fluorescence intensity in response to the first excitation light, in a first wavelength band, EM1ex2 is the fluorescence intensity in response to second excitation light, in the first wavelength band, EM2ex2 is the fluorescence intensity in response to the second excitation light, in a second wavelength band, and EM2ex3 is the fluorescence intensity in response to the third excitation light, in the second wavelength band.

The above-described aspect may further comprise a display unit that displays a distribution of results calculated by the computing unit on the basis of the fluorescence from each part of the observed object.

In the above-described aspect, the display unit may display the results calculated by the computing unit in a conspicuous fashion.

The present invention affords an advantage in that it is possible to precisely detect the distribution of abnormal tissue, such as lesions, in an observed object regardless of the distribution of absorbing material that is present in a living organism.

EXPLANATION OF REFERENCE SIGNS 1,30: fluorescence imaging apparatus
2: light source unit (excitation-light radiating unit)
12: light guide (excitation-light radiating unit)
14: bandpass filter (filter, fluorescence filter)
15: image-acquisition device (light detector)
18: computing unit
35: variable spectrum element (filter)

BEST MODE FOR CARRYING OUT THE INVENTION

Figure 1:
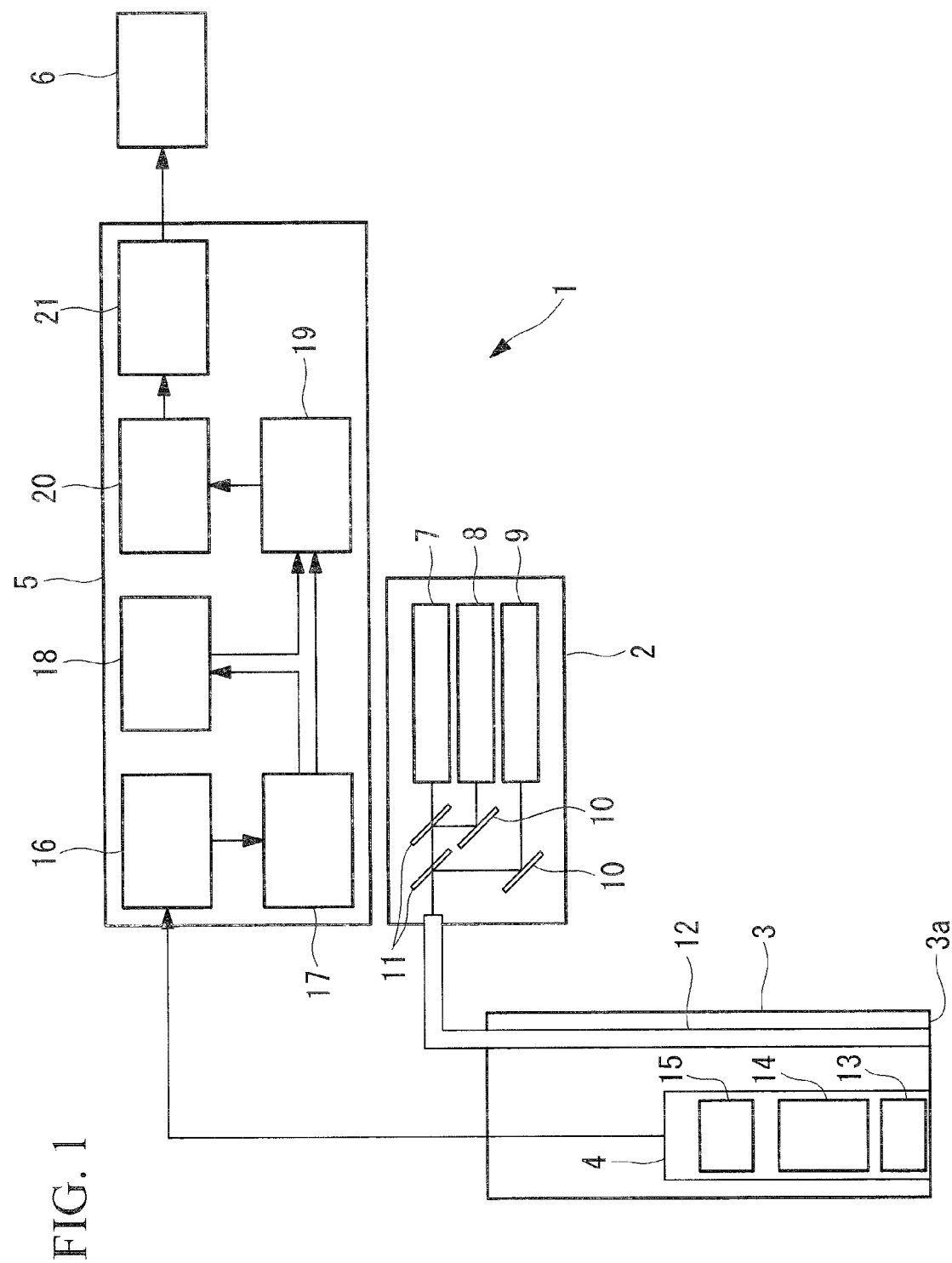
FIG. 1 is a diagram showing the overall configuration of a fluorescence imaging apparatus according to a first embodiment of the present invention.

A fluorescence imaging apparatus 1 according to a first embodiment of the present invention will be described below with reference to FIG. 1 and FIG. 2.

A fluorescence imaging apparatus 1 according to this embodiment includes a light source unit 2 that can emit white light and excitation light of two wavelengths in a switching fashion, an elongated insertion portion 3 that is inserted inside a body cavity, an image-acquisition unit 4 provided in the insertion portion 3, a signal processing unit 5 that processes fluorescence image information detected by the image-acquisition unit 4, and a display unit 6 that displays the output signal from the signal processing unit 5.

The light-source unit 2 is provided with a first laser light source 7 that emits first excitation light with a wavelength $\lambda 1=380$ nm, a second laser light source 8 that emits second excitation light with a wavelength $\lambda 2=430$ nm, a white light source 9 that emits white light, and a mirror 10 and dichroic mirror 11 that combine these into the same optical path.

The insertion unit 3 has extremely narrow outer dimensions allowing it to be inserted into the body cavity of a living organism and is provided, in the interior thereof, with the image-acquisition unit 4 and a light guide 12 that conveys light from the light source unit 2 to a tip 3a thereof.

The image-acquisition unit 4 is provided with an objective lens 13 that collects light incident from the observed object, a fluorescence filter 14 that transmits fluorescence in a specific wavelength band from the light collected by the objective lens 13, and an image-acquisition device 15 that acquires the fluorescence transmitted through the fluorescence filter 14 and converts it to an electrical signal.

Figure 2:
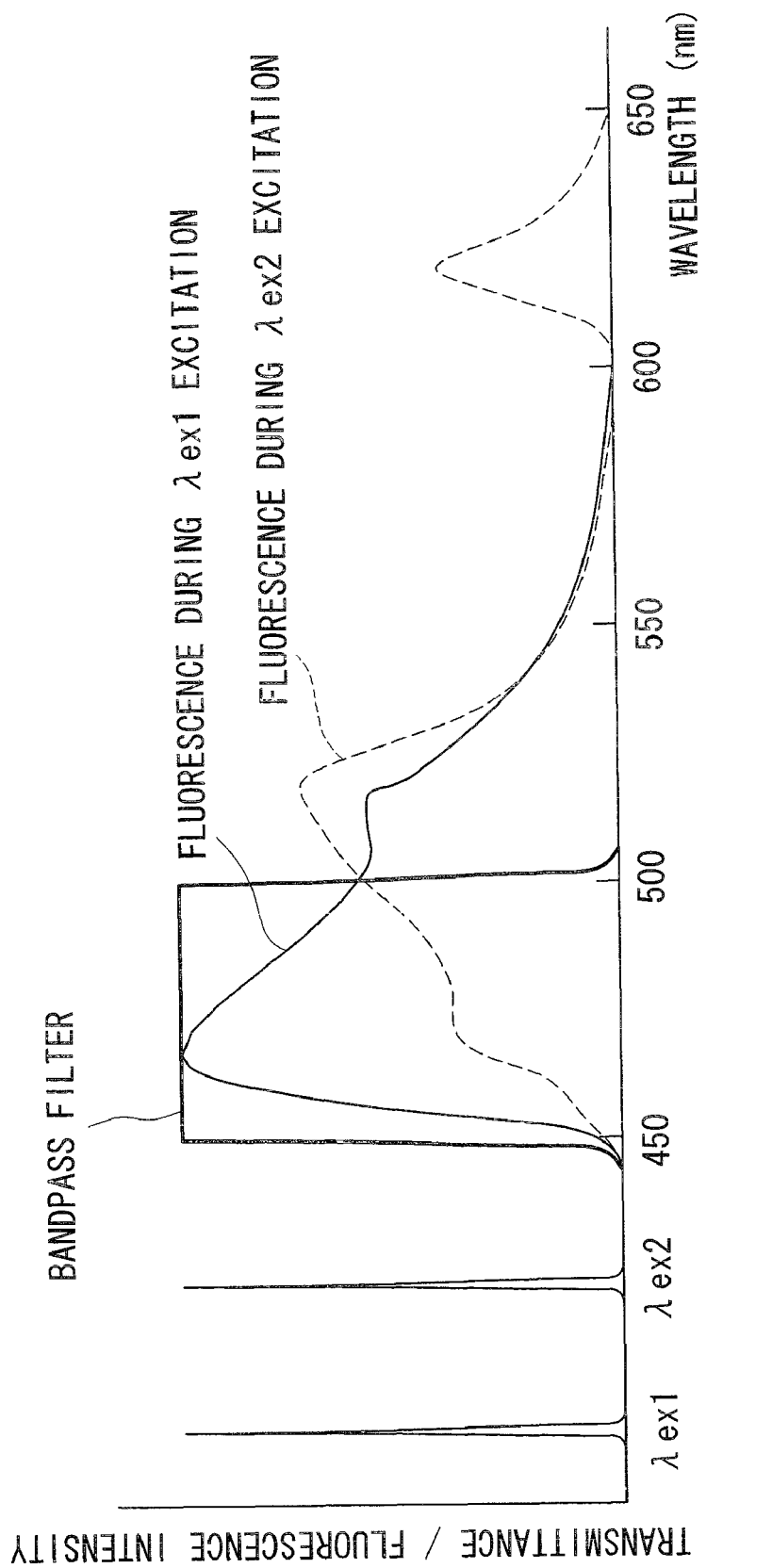
FIG. 2 is a diagram showing an example of the transmittance characteristic of a bandpass filter and wavelength characteristics of excitation light and fluorescence in the fluorescence imaging apparatus in FIG. 1.

The transmission wavelength band of the fluorescence filter 14 is set from 450 nm to 500 nm, inclusive, as shown in FIG. 2.

The signal processing unit 5 includes a video-signal processing unit 16 that generates one reflected-light image and two fluorescence images on the basis of reflected-light intensity information and fluorescence intensity information for both types of excitation light from each part of the observed object, which information is input from the image-acquisition unit 4; a first frame memory 17 that stores the image information generated in the video-signal processing unit 16; a computing unit 18 that performs division processing using the two fluorescence images stored in the first frame memory 17; a second frame memory 19 that stores the respective fluorescence image information subjected to division processing by the computing unit 18 and the reflected-light image; a display processing unit 20 that performs white balance processing on the reflected-light image stored in the second frame memory 19 and that performs superimposition processing on the reflected-light image and the fluorescence images; and an encoder 21 that encodes the superimposed image information and outputs it to the display unit 6.

The ratio (EM1ex1/EM1ex2) of the intensity EM1ex1 of the fluorescence transmitted through the fluorescence filter 14 from among the fluorescence produced by the observed object upon irradiation with the first excitation light emitted from the first laser light source and the intensity EM1ex2 of the fluorescence transmitted through the fluorescence filter 14 from the fluorescence produced by the observed object upon irradiation with the second excitation light emitted from the second laser light source is calculated in the computing unit 18.

The operation of the thus-configured fluorescence imaging apparatus 1 according to this embodiment is described below.

To observe biological tissue using the fluorescence imaging apparatus 1 according to this embodiment, first, the white light source 9 in the light source unit 2 is operated, the insertion portion 3 is inserted into the body cavity, and while checking the reflected-light image, the tip 3a of the insertion portion 3 is placed facing the observation target site in the body cavity. In this state, the first excitation light and the second excitation light are sequentially emitted from the light source unit 2, and the observation target site in the body cavity is irradiated with the first and second excitation light conveyed via the light guide 12.

Reduced nicotinamide adenine dinucleotide (NADH), flavin adenine dinucleotide (FAD), collagen etc., which are naturally occurring autofluorescent substances, are present in biological tissue, and they emit fluorescence due to excitation light from about 300 nm to 500 nm, inclusive. Also, reduced nicotinamide adenine dinucleotide (NADH) and collagen show maximum fluorescence intensity due to excitation light of about 340 nm, and flavin adenine dinucleotide (FAD) does so at about 450 nm. In other words, the maximum-excitation wavelength of reduced nicotinamide adenine dinucleotide (NADH) and collagen is 340 nm, and the maximum-excitation wavelength of flavin adenine dinucleotide (FAD) is 450 nm.

Therefore, mainly reduced nicotinamide adenine dinucleotide (NADH), collagen etc. are excited upon irradiation with the first excitation light, and mainly flavin adenine dinucleotide (FAD) etc. is excited upon irradiation with the second excitation light, emitting their respective fluorescences. FIG. 2 shows wavelength characteristics of the excitation light and fluorescence, as well as the transmittance characteristic of the fluorescence filter 14.

As shown in FIG. 2, the fluorescence produced has a fluorescence spectrum covering a wide range; however, because the fluorescence filter 14 is provided, only fluorescence in the wavelength range from 450 nm to 500 nm, inclusive, contained therein is captured by the image-acquisition device. In other words, the fluorescence produced in the observed object in response to each type of excitation light is input to the video-signal processing unit 16, is structured as two-dimensional fluorescence image information having fluorescence intensity information at each pixel, and is stored in the first frame memory 17.

Then, the two sets of fluorescence image information of the same wavelength band, in response to the excitation light of different wavelengths, which are stored in the first frame memory 17, are subjected to computational processing in the computing unit 18, thereby calculating the fluorescence intensity ratio at each pixel. The reflected-light image stored in the first frame memory 17 is sent, without processing, to the second frame memory 19.

The fluorescence image information subjected to division processing and the reflected-light image are stored in the second frame memory 19. Then, the reflected-light image stored in the second frame memory 19 is subjected to white-balance processing by the display processing unit 20, and after being superimposed with the fluorescence image stored in the second frame memory 19, it is encoded by the encoder 21 and output to the display unit 6, where it is displayed.

With the fluorescence imaging apparatus 1 according to this embodiment, as shown in FIG. 2, the intensities of the two kinds of fluorescence in the transmission wavelength band of the fluorescence filter 14, emitted from the observed object in response to the excitation light of two different wavelengths, differ; however, the fluorescences in the same wavelength band at the same position on the observed object are similarly absorbed by absorbing material present in the observed object because the illumination conditions of the excitation light are the same.

Therefore, by calculating the fluorescence intensity ratio at each pixel using these two sets of fluorescence image information, it is possible to eliminate the influence of absorption due to the absorbing material.

In other words, at a lesion whose naturally bright fluorescence intensity is to be acquired, it was difficult to distinguish between a lesion and a normal area in a fluorescence image due to single excitation light because the fluorescence intensity is reduced due to the influence of the absorbing material; however, with the fluorescence imaging apparatus 1 according to this embodiment, the influence of the absorbing material can be removed, enabling accurate distinction between a lesion and a normal area. Therefore, an advantage is afforded in that the diagnostic ability can be enhanced. As the light source that excites fluorescence, besides a laser light source, an LED or a combination of a white-light source and a band-pass filter may also be used.

Next, a fluorescence imaging apparatus 30 according to a second embodiment of the present invention will be described below with reference to FIGS. 3 to 8.

In the description of this embodiment, parts having the same configuration as those in the fluorescence imaging apparatus 1 according to the first embodiment described above are assigned the same reference numerals, and a description thereof is omitted.

Figure 3:
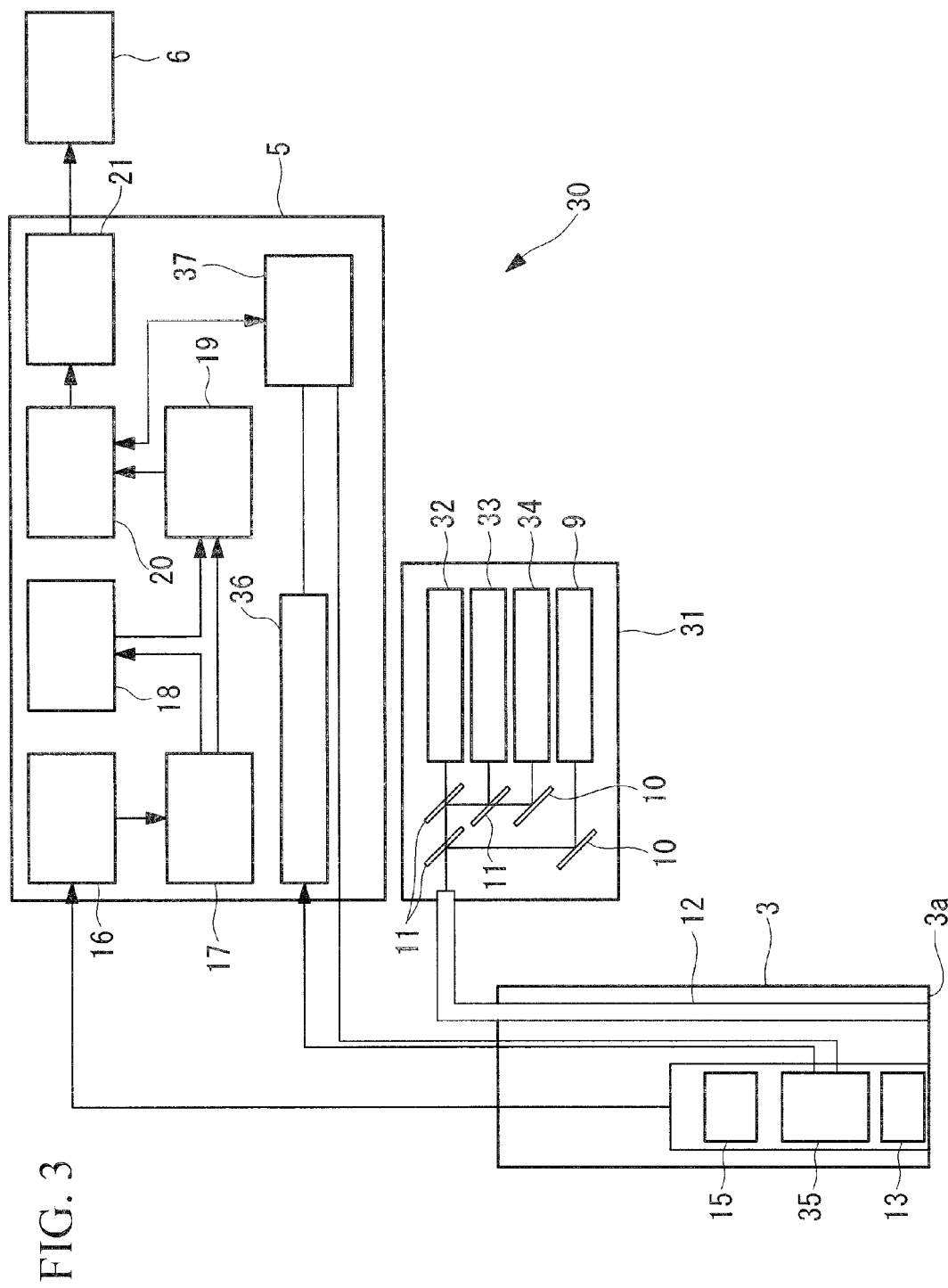
FIG. 3 is a diagram showing the overall configuration of a fluorescence imaging apparatus according to a second embodiment of the present invention.
Figure 4:
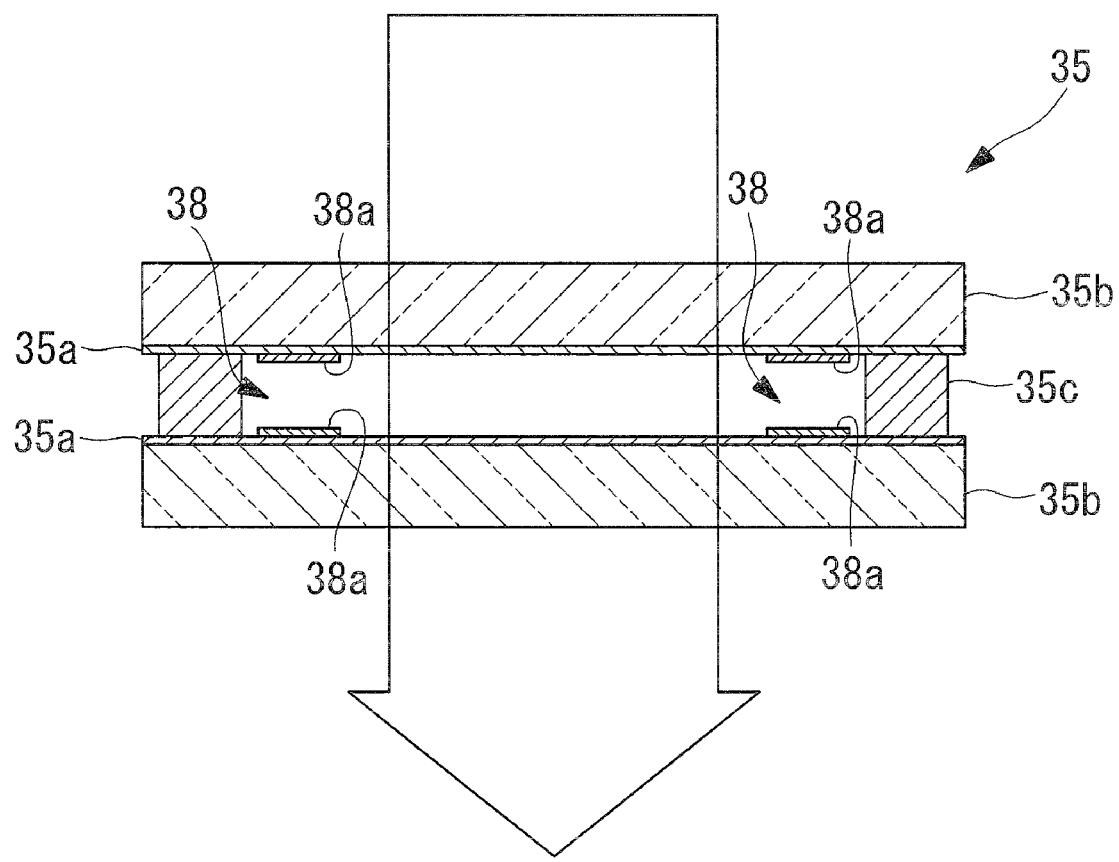
FIG. 4 is a longitudinal sectional view showing a variable spectrum element provided in the fluorescence imaging apparatus in FIG. 3.

As shown in FIG. 3, the fluorescence imaging apparatus 30 according to this embodiment differs from the fluorescence imaging apparatus 1 according to the first embodiment in that a light source unit 31 has first to third laser light sources 32 to 34, an etalon-type variable spectrum element 35 such as that shown in FIG. 4 is employed instead of the fluorescence filter 14, and a distance-signal processing unit 36 and a control unit 37 for the variable spectrum element 35 are provided in the signal processing unit 5.

The first laser light source 32 emits first excitation light with a wavelength $\lambda 1=380$ nm. The second laser light source 33 emits second excitation light with a wavelength $\lambda 2=400$ nm. The third laser light source 34 emits third excitation light with a wavelength $\lambda 3=430$ nm.

Wavelength $\lambda 2$ is set to fall in the wavelength band between the maximum-excitation wavelength of NADH or collagen and the maximum-excitation wavelength of FAD. In this embodiment, as a particularly preferable example, 400 nm, which is a wavelength approximately in the middle of the these two maximum-excitation wavelengths, is selected as the wavelength of the second excitation light radiated from the second laser light source 33.

As shown in FIG. 4, the variable spectrum element 35 includes two optical substrates 35b that face each other with a distance therebetween and that are provided with reflective films 35a on the opposing surfaces, actuators 35c that change the distance between these optical substrates 35b, and sensors 38 provided on the opposing surfaces of the optical substrates 35b. The actuators 35c are formed of, for example, piezoelectric devices, and a plurality of them are provided at intervals in the circumferential direction of the optical substrates 35b. The sensors 38, a plurality of which are provided, for example, at intervals in the circumferential direction on each of the optical substrates 35b, include mutually opposing sensor electrodes 38a, and the distance between the optical substrates 35b is detected by detecting a change in electrostatic capacitance formed between the sensor electrodes 38a.

Figure 5:
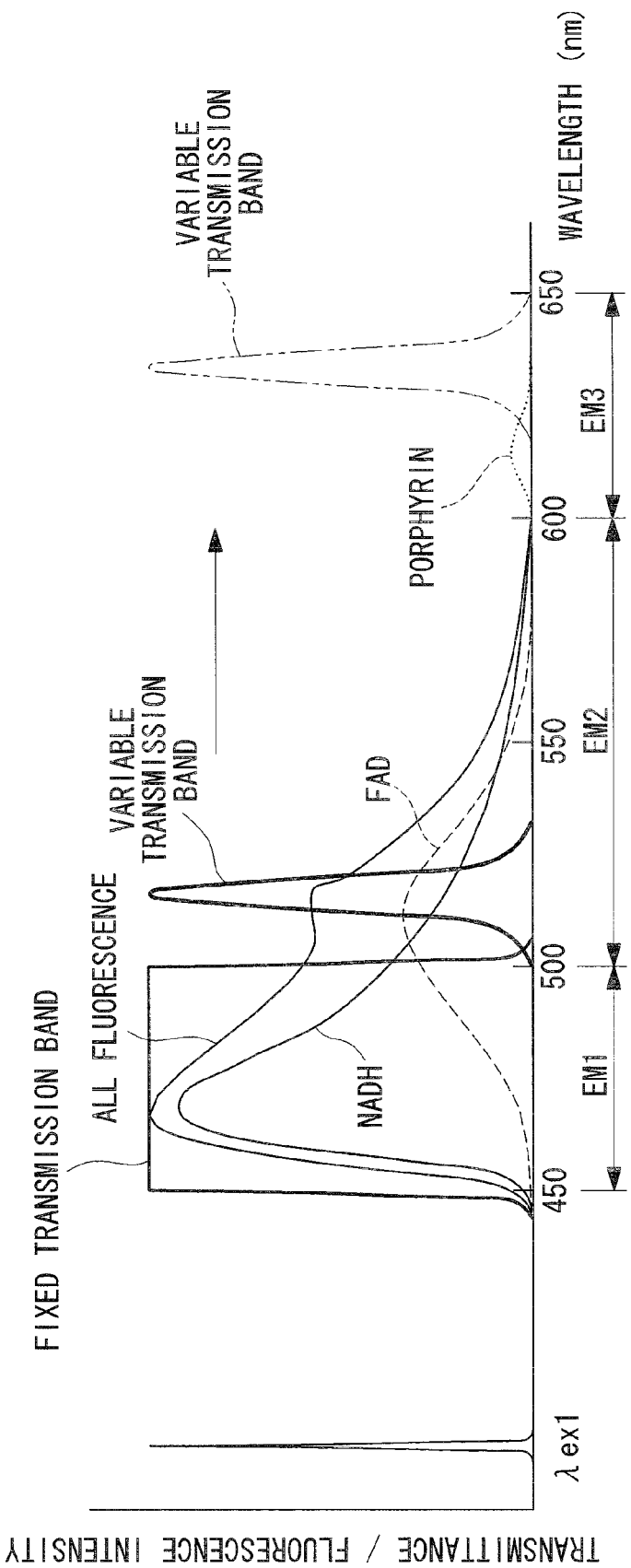
FIG. 5 is a diagram showing an example of the transmittance characteristic of the variable spectrum element in FIG. 4, and the wavelength characteristics of first excitation light and fluorescence in response thereto.
Figure 6:
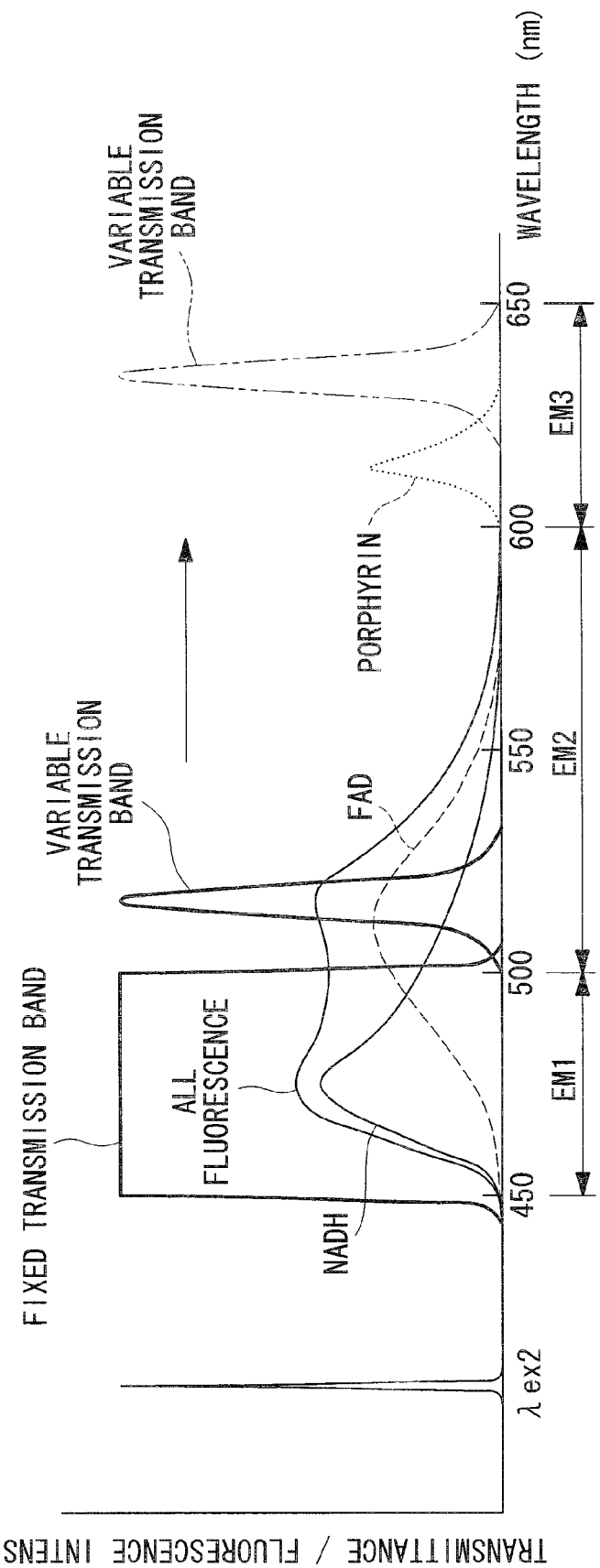
FIG. 6 is a diagram showing an example of the transmittance characteristic of the variable spectrum element in FIG. 4, and the wavelength characteristics of second excitation light and fluorescence in response thereto.
Figure 7:
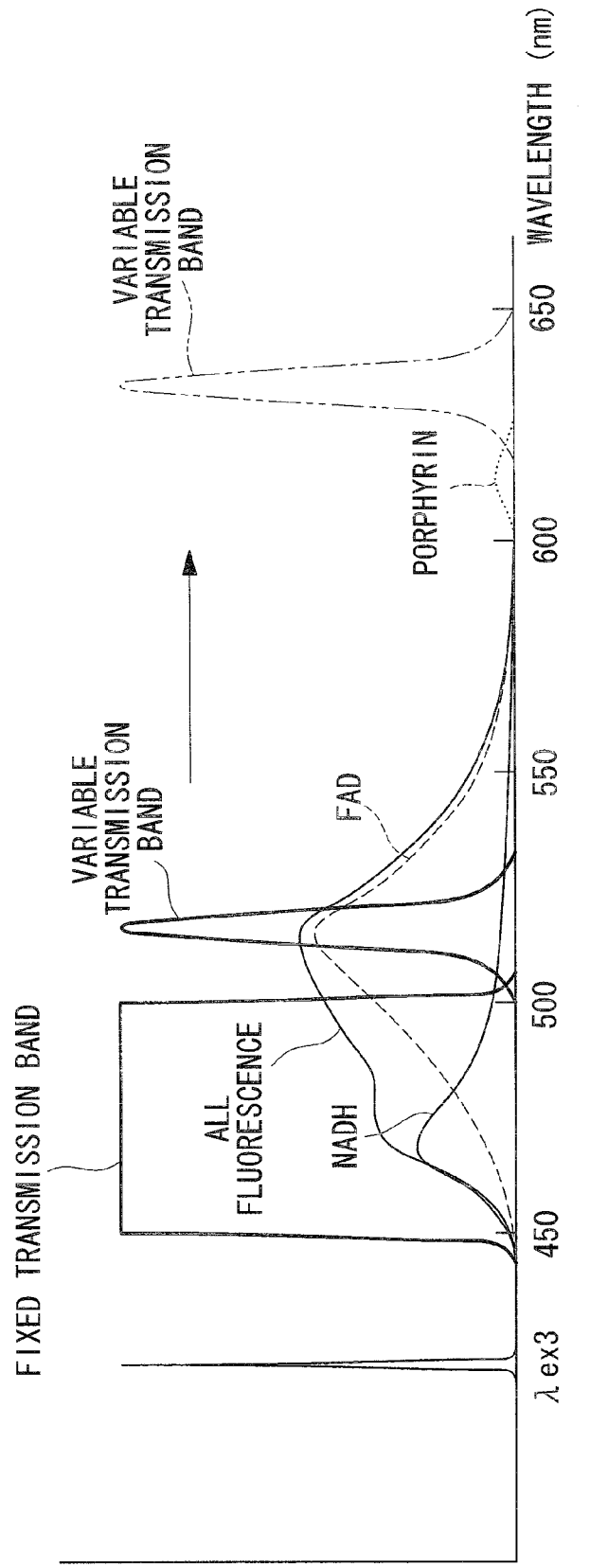
FIG. 7 is a diagram showing an example of the transmittance characteristic of the variable spectrum element in FIG. 4, and the wavelength characteristics of third excitation light and fluorescence in response thereto.

As shown in FIGS. 5 to 7, the variable spectrum element 35 has a wavelength characteristic having a fixed transmission band and a variable transmission band. The fixed transmission band is set in a wavelength band from 450 nm to 500 nm, inclusive, to always allow passage of fluorescence in this wavelength band. The variable transmission band is set, for example, in a wavelength band from 500 nm to 650 nm, inclusive, and by changing the distance between the optical substrates 35b by operating the actuators 35c, it is possible to shift the transmission band, having a suitably narrow width relative to the entire wavelength band.

The distance-signal processing unit 36 provided in the signal processing unit 5 amplifies the detected signal received from the sensor electrodes 38a and subjects the amplified signal to noise-removal processing and A/D conversion. The control unit 37 obtains the distance between the optical substrates 35b on the basis of the signal input from the distance-signal processing unit 36 and outputs a command signal to the actuators 35c so that the distance becomes a desired distance. By controlling the plurality of actuators 35c provided in the circumferential direction on the basis of the signals detected by the plurality of sensors 38 similarly provided in the circumferential direction, it is possible to adjust the distance while precisely maintaining the optical substrates 35b parallel to each other.

Then, by outputting the command signal to the actuators 35c, the control unit 37 gradually varies the distance between the optical substrates 35b, thus gradually shifting the transmission band in the variable transmission band.

As the fluorescence image information EM1ex1, EM1ex2, and EM1ex3 for a first wavelength band of 450 nm to 500 nm, inclusive, the video-signal processing unit 16 stores the fluorescence intensities obtained by respectively radiating the first to third excitation light in the first frame memory 17 without processing.

Additionally, for a second wavelength band, for example, 500 nm to 600 nm, inclusive, the values obtained by integrating, at each pixel, the fluorescence intensities acquired during shifting of the transmission band in the second wavelength band while respectively radiating the first to third excitation light are stored in the first frame memory 17 as the fluorescence image information EM2ex1, EM2ex2, and EM2ex3 for the wavelength band from 500 nm to 600 nm, inclusive, by taking the differences with respect to the fluorescence image information EM1ex1, EM1ex2, and EM1ex3.

Additionally, for a third wavelength band, for example, 600 nm to 650 nm, inclusive, the values obtained by integrating, at each pixel, the fluorescence intensities acquired during shifting of the transmission band in the third wavelength band while respectively radiating the first to third excitation light are stored in the first frame memory 17 as the fluorescence image information EM3ex1, EM3ex2, and EM3ex3 for the wavelength band from 600 nm to 650 nm, inclusive, by taking the differences with respect to the fluorescence image information EM1ex1, EM1ex2, and EM1ex3.

Ratios of these sets of fluorescence image information, for example, P=(EM1ex1/EM1ex3), Q=(EM2ex3/EM2ex1), and R=(EM3ex2/EM3ex1)×(EM3ex2/EM3ex3), are calculated in the computing unit 18.

Figure 8:
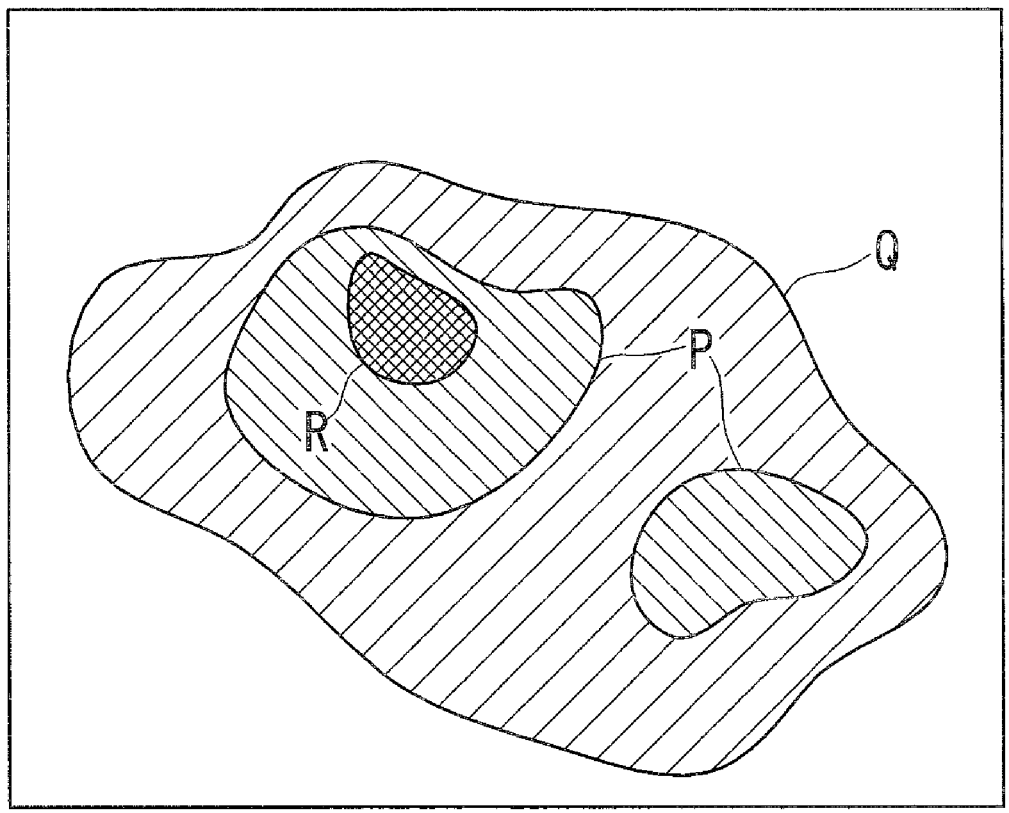
FIG. 8 is a diagram showing an example of a fluorescence image displayed by the fluorescence imaging apparatus in FIG. 3.

The fluorescence image information ratios calculated in the computing unit 18 are stored in the second frame memory 19, are subjected to superimposition processing by the display processing unit 20, and are displayed by the display unit 6, via the encoder 21. As the display method, for example, as shown in FIG. 8, it is preferable to draw the contour of each region, or to change the color thereof, so that the region of each fluorescence image information ratio is made distinct.

With the thus-configured fluorescence imaging apparatus 30 according to this embodiment, in each wavelength band in the plurality of wavelength bands, the ratio of the fluorescence intensities produced when exciting with excitation light of different wavelengths is calculated, and in each respective wavelength band, it is possible to acquire a fluorescence image in which the influence of absorption due to an absorbing material is eliminated at each position in the image. Accordingly, it is possible to more precisely distinguish between a normal area and a lesion.

In this embodiment, the fluorescence image information ratio (EM3ex2/EM3ex1)×(EM3ex2/EM3ex3) is calculated and displayed. Accordingly, the lesion is emphasized; instead of this, however, either (EM3ex2/EM3ex1) or (EM3ex2/EM3ex3) may be calculated and displayed.

Additionally, as the fluorescence image information ratio, (EM1ex1/EM1ex2)/(EM2ex3/EM2ex2) and (EM3ex2/EM3ex1)>1 and (EM3ex2/EM3ex3)>1 may be displayed as operators. As the light source for exciting fluorescence, besides a laser light source, an LED or a combination of a white-light source and a bandpass filter may be used, and for the fluorescence transmission band, a plurality of bandpass filters may be used.

Figure 9A:
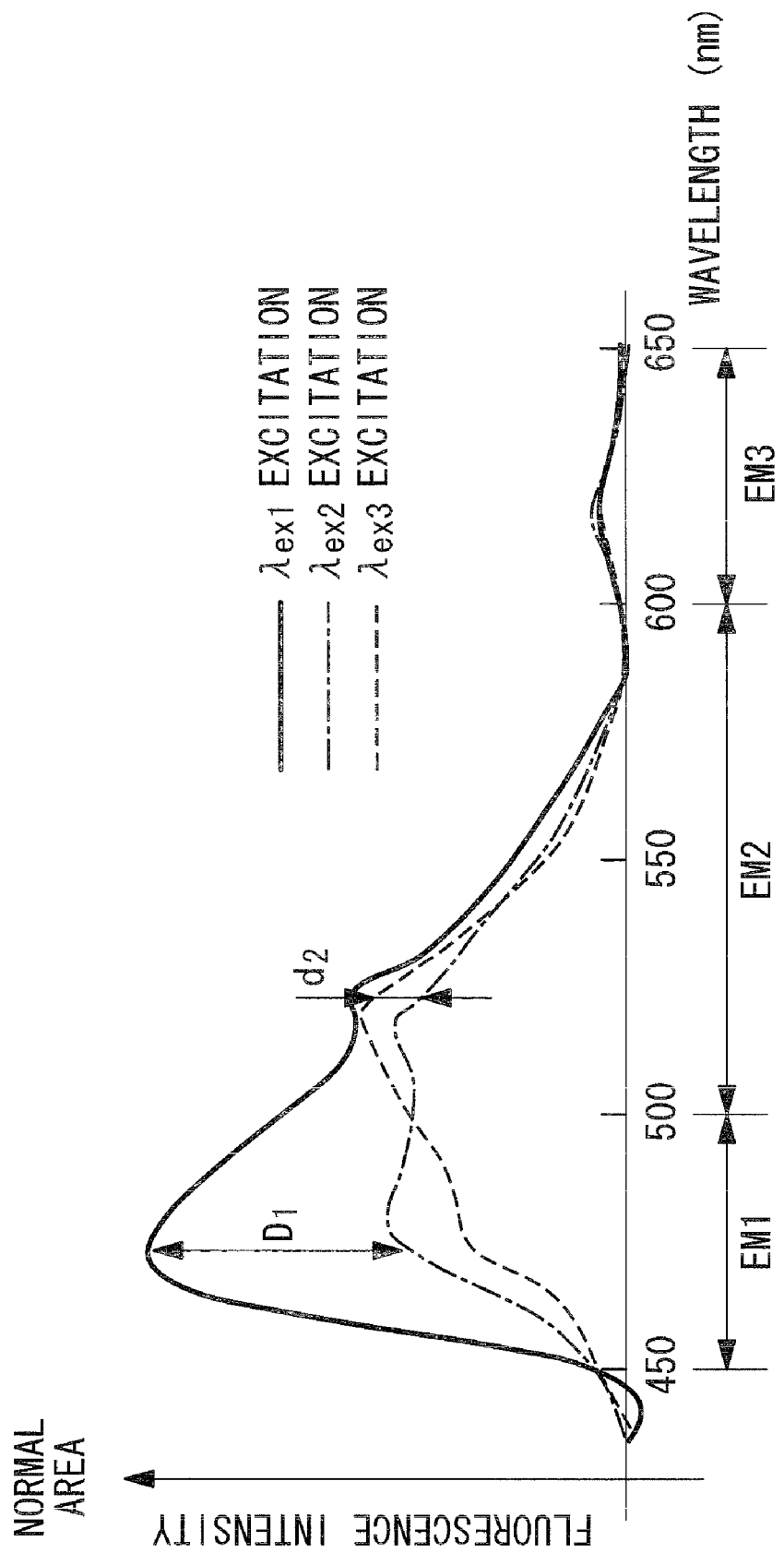
FIG. 9A is a diagram showing an example of the transmittance characteristic of the variable spectrum element and the wavelength characteristics of fluorescence from a normal area in response to the first to third excitation light, for explaining a modification of the fluorescence imaging apparatus in FIG. 3.
Figure 9B:
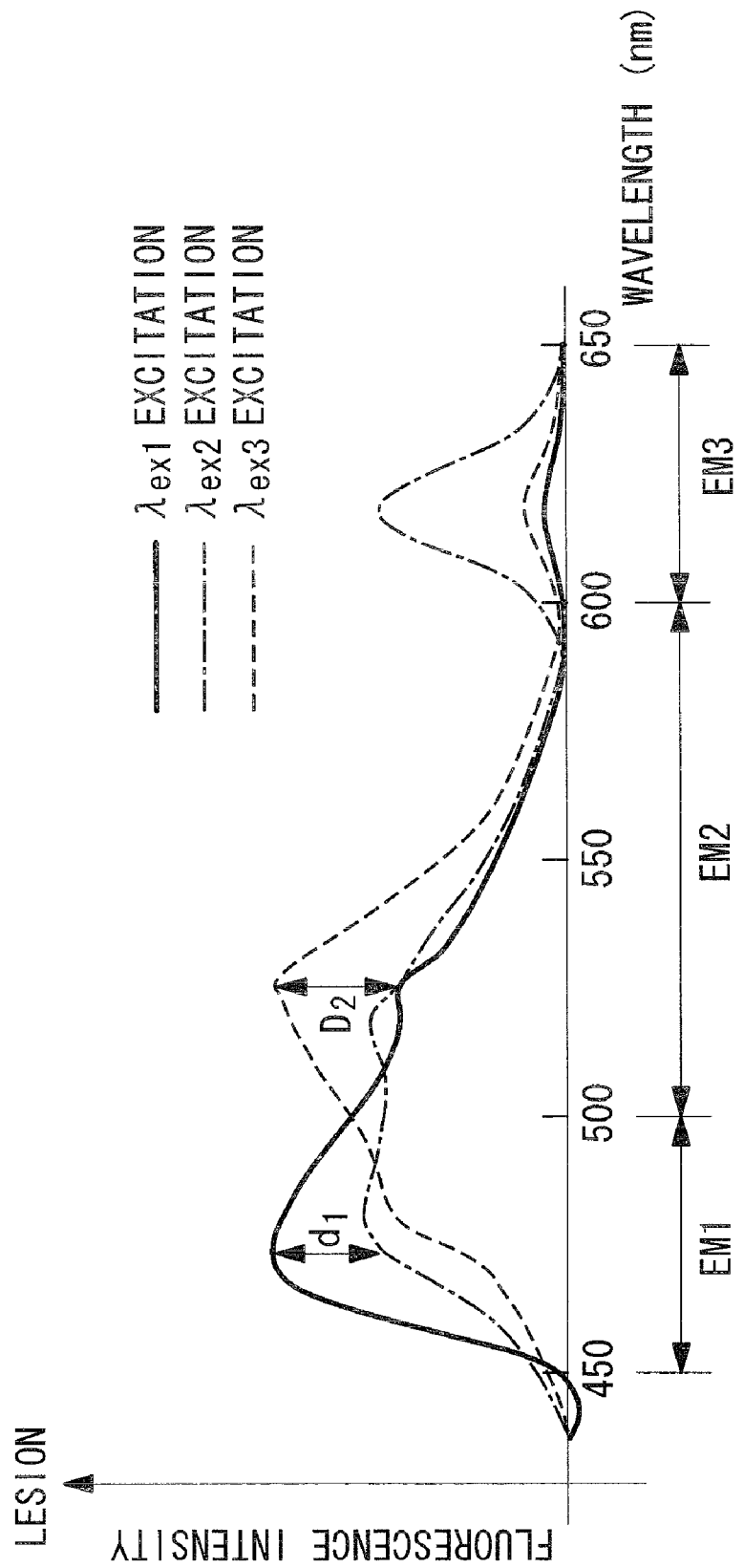
FIG. 9B is a diagram showing an example of the transmittance characteristic of the variable spectrum element and the wavelength characteristics of fluorescence from a lesion in response to the first to third excitation light, for explaining a modification of the fluorescence imaging apparatus in FIG. 3.

FIG. 9A shows wavelength characteristics of the fluorescence from a normal area when irradiated with the first to third excitation light, and FIG. 9B shows wavelength characteristics of the fluorescence from a lesion when irradiated with the first to third excitation light.

As shown in FIG. 9A and FIG. 9B, in the first wavelength band from 450 nm to 500 nm, inclusive, at the fluorescence differences (reference signs $D_1$ and $d_1$) when the first excitation light and the second excitation light are radiated, there is a large difference $D_1-d_1$ between the lesion and the normal area. Also, in the second wavelength band from 500 nm to 600 nm, inclusive, at the fluorescence differences (reference signs $D_2$ and $d_2$) when the second excitation light and the third excitation light are radiated, there is a large difference $D_2-d_2$ between the lesion and the normal area.

Therefore, by displaying (EM1ex1/EM1ex2)/(EM2ex3/EM2ex2), which is a calculated value showing a characteristic difference in the spectral optical characteristics of the lesion and the normal area, it is possible to display the lesion more conspicuously.

In addition, in the third wavelength band from 600 nm to 650 nm, inclusive, because there is no difference in the fluorescence produced from the normal area even though the excitation light is different, by displaying (EM3ex3/EM 3ex1)>1 and (EM3ex2/EM3ex3)>1, it is possible to display the lesion conspicuously.

The invention claimed is:

1. A fluorescence imaging apparatus comprising:
   an excitation-light radiating unit that irradiates an observed object with excitation light of a plurality of wavelengths;
   a filter that transmits fluorescence in a specific wavelength band including fluorescence of a plurality of wavelengths produced by the excitation light of the plurality of wavelengths, the specific wavelength band encompassing a portion of the entire range of all fluorescence produced from among fluorescence produced from the observed object in response to the excitation light radiated from the excitation-light radiating unit;
   a light detector that detects the fluorescence transmitted through the filter; and
   a computing unit that calculates a fluorescence intensity ratio in the same wavelength band as the specific wavelength band_in response to the excitation light of the plurality of wavelengths, which is detected by the light detector.

2. A fluorescence imaging apparatus according to claim 1, wherein the filter transmits fluorescence of a plurality of wavelength bands, and the computing unit calculates the fluorescence intensity ratio in each wavelength band.

3. The fluorescence imaging apparatus according to claim 2, wherein the filter is formed of a variable spectrum element that can change the wavelength band at which the fluorescence is transmitted.

4. A fluorescence imaging apparatus according to claim 1, wherein the wavelength of at least one kind of excitation light of the excitation light of the plurality of wavelengths is contained in a wavelength band between a maximum-excitation wavelength of a first substance excited by the excitation light and a maximum-excitation wavelength of a second substance that differs from the first substance.

5. A fluorescence imaging apparatus according to claim 4, wherein the first substance is collagen or NADH, and the second substance is FAD.

6. A fluorescence imaging apparatus according to claim 4, wherein the wavelength of at least one kind of excitation light in the excitation light of the plurality of wavelengths contains a wavelength with a middle value between the maximum-excitation wavelength of the first substance excited by the excitation light and the maximum-excitation wavelength of the second substance that differs from the first substance.

7. A fluorescence imaging apparatus according to claim 5, wherein the pass band of the filter that transmits the fluorescence with a specific wavelength band contains a wavelength at which the fluorescence intensity of collagen, NADH, FAD, or porphyrin is maximized.

8. A fluorescence imaging apparatus according to claim 3, wherein the variable spectrum element shifts a transmission band that is narrower than the wavelength band for detecting fluorescence, and the computing unit calculates the ratio using integrated values of the fluorescence intensities detected by the light detector at each shifted position of the transmission band.

9. A fluorescence imaging apparatus according to claim 1, wherein the computing unit calculates the fluorescence intensity ratio according to the following expression:

$$(EM1ex1/EM1ex2)/(Em2ex3/EM2ex2)$$

where
- $EM1ex1$ is the fluorescence intensity in response to the first excitation light, in a first wavelength band which is part of the specific wavelength band that passes through the filter,
- $EM1ex2$ is the fluorescence intensity in response to second excitation light, in the first wavelength band which is part of the specific wavelength band that is transmitted through the filter,
- $EM2ex2$ is the fluorescence intensity in response to the second excitation light, in a second wavelength band which is part of the specific wavelength band that is transmitted through the filter, and
- $EM2ex3$ is the fluorescence intensity in response to the third excitation light, in the second wavelength band which is part of the specific wavelength band that is transmitted through the filter, and the wavelength of the first excitation light<the wavelength of the second excitation light<the wavelength of the third excitation light.

10. A fluorescence imaging apparatus according to claim 1, further comprising a display unit that displays a distribution of results calculated by the computing unit on the basis of the fluorescence from each part of the observed object.

11. A fluorescence imaging apparatus according to claim 10, wherein the display unit displays the results calculated by the computing unit in a conspicuous fashion.

12. The fluorescence imaging apparatus of claim 1, wherein the specific wavelength band encompasses a portion of about 50 nm of the entire range of all wavelengths produced from the observed object.

* * * * *